US006469070B1

(12) United States Patent
Vanden Berghe

(10) Patent No.: US 6,469,070 B1
(45) Date of Patent: Oct. 22, 2002

(54) TOPICAL MEDICAMENT COMPRISING PHENOLIC BIOCIDE AND CHOLINE

(75) Inventor: Dirk Vanden Berghe, Laarne (BE)

(73) Assignee: Biominerals, N.V., Destelbergen (BE)

( * ) Notice: Subject to any disclaimer, the term of this patent is extended or adjusted under 35 U.S.C. 154(b) by 0 days.

(21) Appl. No.: 09/180,677

(22) PCT Filed: May 14, 1997

(86) PCT No.: PCT/GB97/01306

§ 371 (c)(1),
(2), (4) Date: Aug. 11, 1999

(87) PCT Pub. No.: WO97/42942

PCT Pub. Date: Nov. 20, 1997

(30) Foreign Application Priority Data

May 15, 1996 (GB) ................................ 9610122

(51) Int. Cl.$^7$ ............................................. A61K 31/045
(52) U.S. Cl. ..................... 514/738; 514/728; 514/731
(58) Field of Search ................... 514/731, 727, 514/738

(56) References Cited

U.S. PATENT DOCUMENTS

| | | | | | |
|---|---|---|---|---|---|
| 4,699,136 A | * | 10/1987 | Krauser | ................ | 128/203.22 |
| 4,895,727 A | * | 1/1990 | Allen | ................ | 424/642 |
| 5,446,070 A | * | 8/1995 | Mantelle | | |
| 5,565,439 A | * | 10/1996 | Piazza et al. | ................ | 514/110 |
| 5,654,312 A | * | 8/1997 | Andrulis, Jr. et al. | ....... | 514/279 |
| 5,690,954 A | * | 11/1997 | Illum | | |
| 5,703,063 A | * | 12/1997 | Chasalow | | |
| 5,834,513 A | * | 11/1998 | Ptchelintsev et al. | ....... | 514/561 |
| 5,955,109 A | * | 9/1999 | Won et al. | ................ | 424/501 |

FOREIGN PATENT DOCUMENTS

| | | | | |
|---|---|---|---|---|
| BE | 871192 | 2/1979 | | |
| CN | 1095587 | 11/1994 | ............ | A61K/7/48 |
| EP | 0679390 | 11/1995 | ............ | A61K/9/12 |
| WO | 8102673 | 10/1981 | .......... | A61K/31/65 |

OTHER PUBLICATIONS

Knood, Callus and plantar wart remover, Abstract of Patent, BE 871192, Feb. 1979.*

Abstract, Database EPODOC. EPO XP002036477. CN 1 095 587, 1994.

* cited by examiner

Primary Examiner—William R. A. Jarvis
Assistant Examiner—Vickie Kim
(74) Attorney, Agent, or Firm—Webb Ziesenheim Logsdon Orkin & Hanson, P.C.

(57) ABSTRACT

A topical medicament for the treatment of warts, corns and verrucae including a phenolic biocide, which is preferably a compound of formula (I), in which n is from 0 to 19, in combination with choline or a derivative or a salt thereof. A method for treatment of warts, corns and verrucae is also provided which includes the steps of applying the topical medicament to the warts, corns and verrucae.

15 Claims, No Drawings

TOPICAL MEDICAMENT COMPRISING PHENOLIC BIOCIDE AND CHOLINE

This application is 371 of PCT/GB97/01306 filed May 14, 1997 which claims priority benefit to United Kingdom 9610122.5 filed May 15, 1996.

BACKGROUND OF THE INVENTION

1. Field of the Invention

The present invention relates to the preparation of topical medicaments for the treatment of warts and related conditions. In particular it relates to the use of phenolic biocidal compounds to prepare such medicaments.

2. Description of the Related Art

A wide range of generally non-life threatening but highly irritating conditions affect both the human and animal skin. These include warts, corns and verrucae.

A range of compounds has been suggested for use in the treatment of such conditions, however they all suffer from one or more drawbacks, including lack of efficacy or excessive irritancy. Thus there is a continuing need for a treatment of warts, corns and verrucae which is both effective and non-irritant.

We have now found that a range of phenolic biocidal compounds are particularly effective at treating such conditions and that their irritancy can be sufficiently reduced by combination with choline or derivatives thereof.

SUMMARY OF THE INVENTION

According to the invention there is provided the use of phenolic biocide, which is preferably a compound of formula I <img>HO-C6H3(OH)-(CH2)nCH3</img> in which n is from 0 to 19, in combination with choline or a derivative or a salt thereof, for the preparation of a topical medicament for the treatment of warts, corns or verrucae.

There is further provided a topical medicament comprising a phenolic biocide, which is preferably a compound of formula I in which n is from 0 to 19, and choline or a derivative or a salt thereof.

DETAILED DESCRIPTION OF THE PREFERRED EMBODIMENTS

Preferably in the topical medicaments of the invention the phenolic biocide and the choline or derivative or salt thereof are in intimate admixture.

Preferably in the compound of formula I n is 3 to 13.

Most preferably the compound of formula I is 4-hexylresorcinol.

The compound of formula I is preferably used at a concentration of from 0.01 to 20% by weight, more preferably 0.1 to 5% w/w, most preferably 0.2 to 3.0% w/w Preferred derivatives of choline include lecithin, glycerophosphocholine and acetylcholine. Preferred salts of choline include choline chloride, choline phosphate, choline iodide and choline bromide, most preferably choline chloride.

The concentration of choline, or a derivative, other than lecithin, or a salt thereof, in the topical medicaments of the invention is preferably from 0.01 to 20% w/w, more preferably 0.1 to 5% w/w, most preferably 0.2 to 3.0% w/w. When lecithin is used in the topical medicaments of the invention the concentration is preferably 0.2 to 30% w/w, most preferably 1 to 10% w/w.

We have also found that the inclusion of a surfactant in the topical medicaments of the invention may lead to improved activity versus warts, corns and verrucae.

Therefore the topical medicaments of the invention preferably further comprise a surfactant. The surfactant is preferably an anionic surfactant, most preferably N-lauroylsarcosine or a salt thereof. The concentration of surfactant in the topical medicaments of the invention is preferably from 0.1 to 5% w/w, most preferably from 0.2 to 3% w/w.

The topical medicaments of the invention may also comprise further biocidal agents in addition to the compounds of formula I. Preferably these further biocides are quaternary ammonium compounds or phenolic compounds. More preferably the further biocide is trimethyltetradecylammonium bromide (cetrimide).

The concentration of the further biocide in the topical medicaments of the invention is preferably from 0.1 to 5% w/w, most preferably from 0.2 to 3% w/w.

The topical medicaments of the invention may also comprise inositol. The concentration of inositol is preferably from 0.05 to 20% w/w; most preferably from 0.2 to 5% w/w.

The topical medicaments of the invention may be applied to any part of the body surface, including mucous membranes. The topical medicaments of the invention may be applied in conventional cream or ointment form; may be applied predispersed onto a dressing or plaster; or in conventional topical sustained release devices.

The topical medicaments of the invention may be formulated using any suitable aqueous or non-aqueous vehicles, the preferred vehicles are paraffin, Vaseline (a trademark), Lanette N (a mixture of cetearyl alcohol and sodium cetearyl alcohol sulphate), and non aqueous polymer compositions including nitrocellulose, Collodion and Carboset (available from B. F. Goodrich) and ethylcellulose. Preferably the vehicle is non-aqueous.

The topical medicaments of the invention may be manufactured using any conventional manufacturing processes, however it is preferred that the phenolic biocide and the choline or derivative or salt thereof are in intimate admixture. This may be ensured either by homogenous premixing of the phenolic biocide and the choline or derivative or salt thereof before dispersion in the vehicle, or by thorough dispersion of both ingredients directly into the vehicle.

Further according to the invention, there is provided a topical medicament comprising i) 0.01 to 20% w/w of a compound of formula I in which n is from 0 to 19, ii) 0.01 to 20% w/w choline, or a derivative or a salt thereof, and iii) 0.1 to 5% w/w of a surfactant.

The invention will now be illustrated by reference to the following examples.

EXAMPLE 1

The following formulation is prepared

| | |
|---|---|
| Hexylresorcinol (Sigma H6250) | 1.8 g |
| Choline chloride (Sigma C1879) | 1.0 g |
| White Vaseline | 97.2 g |

The hexylresorcinol and choline chloride are pulverised and mixed together, then added to the Vaseline and homogenised by rapid stirring with a spatula.

EXAMPLE 2

The following formulation is prepared

| | |
|---|---|
| Hexylresorcinol (Sigma H6250) | 1.8 g |
| Choline chloride (Sigma C1879) | 1.0 g |
| N-lauroylsarcosine sodium (Sigma L5000) | 1.8 g |
| White Vaseline | 95.4 g |

The hexylresorcinol, choline chloride and N-lauroylsarcosine sodium are pulverised and mixed together, then added to the Vaseline and homogenised by rapid stirring with a spatula.

COMPARATIVE EXAMPLE 1

Example 1 is Repeated with the Following Formula

| | |
|---|---|
| Hexylresorcinol (Sigma H6250) | 1.8 g |
| White Vaseline | 98.2 g |

COMPARATIVE EXAMPLE 2

Example 2 is Repeated with the Following Formula

| | |
|---|---|
| Hexylresorcinol (Sigma H6250) | 1.8 g |
| N-lauroylsarcosine sodium (Sigma L5000) | 1.8 g |
| White Vaseline | 96.4 g |

EXAMPLE 3

The following formulation is prepared

| | |
|---|---|
| Hexylresorcinol (Sigma H6250) | 1.8 g |
| N-lauroylsarcosine (Sigma L5000) | 1.8 g |
| Cetrimide (Federa P68 1932) | 0.5 g |
| Choline chloride (Sigma C1879) | 1.0 g |
| Myo-inositol (Sigma I 5125) | 0.25 g |
| White Vaseline | 94.65 g |

All the powders are pulverised and mixed together. Vaseline is added and the mixture is homogenised by rapid stirring with a spatula.

EXAMPLE 4

Corn Treatment

A female patient having an irritant corn on the outside of the small toe (previously resistant to all conventional treatments for at least 5 years) was treated by application of the composition of Example 3 to the corn. The application was of a liberal sample twice daily for 10 days and once daily for 5 days. The corn was covered by a conventional corn plaster between applications. After 15 days the corn was completely healed with no scarring and no pain. There has been no relapse after 3 months.

EXAMPLE 5

Verrucae Treatment

A male patient having a verruca on the sole of one foot was treated by application of the composition of Example 3 to the verruca. The application was of from 0.1 to 0.2 ml of the composition twice daily for 21 days. The verruca was covered with a conventional plaster between applications. After 21 days the verruca was healed (removed) leaving no pain or scarring. No relapse has occurred after 12 months.

EXAMPLE 6

The ability of choline chloride to reduce the irritant properties of hexylresorcinol alone or in combination with N-lauroylsarcosine sodium (an anionic surfactant) was tested by the following procedure.

Four 2 cm$^2$ sites were marked at intervals along the intact skin of the forearm of an adult human female. Samples of each of Examples 1 and 2 and comparative examples 1 and 2 were applied liberally to each site (one treatment per site). Application was carried out twice daily for 3 days (six applications in all). The sites were occluded using adhesive plasters between applications. The appearance of the sites on the arm was inspected 72 hours after the first application with the following results.

| | |
|---|---|
| Comparative Example 1 | blistering, skin irritation |
| Example 1 | no blistering, skin unmarked |
| Comparative Example 2 | blistering, skin irritation |
| Example 2 | no blistering, skin mostly clear, reduced irritation. |

What is claimed is:

1. A method for treatment of warts, corns and verrucae comprising applying to the wart, corn or verrucae a topical medicament consisting essentially of a topical medicament including an intimate admixture of a phenolic biocide and a substance selected from the group consisting of choline and a salt thereof, other than lecithin or a lecithin salt, wherein said phenolic biocide is a compound of formula I

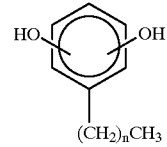

in which n is from 0 to 19.

2. The method as claimed in claim 1, wherein the phenolic biocide is 4-hexylresorcinol.

3. The method as claimed in claim 1, wherein the topical medicament further comprises a surfactant.

4. A topical medicament, consisting essentially of an intimate admixture:
   i) a phenolic biocide of formula I

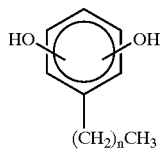

in which n is from 0 to 19; and
   ii) a substance selected from the group consisting of choline and a salt thereof, other than lecithin or a lecithin salt.

5. A topical medicament as claimed in claim 4, wherein the topical medicament further comprises a surfactant.

6. A topical medicament as claimed in claim 4, wherein the phenolic biocide is 4-hexylresorcinol.

7. A topical medicament as claimed in claim 4, wherein the choline salt is selected from the group consisting of choline chloride, choline phosphate, choline iodide and choline bromide.

8. A topical medicament as claimed in claim 5, wherein the surfactant is N-lauroylsarcosine or a salt thereof.

9. A topical medicament as claimed in claim 5, comprising:
   i) 0.01 to 20% w/w of the phenolic biocide;
   ii) 0.01% to 20% w/w of the choline, or the salt thereof; and
   iii) 0.1 to 5% w/w of the surfactant.

10. A topical medicament as claimed in claim 4, comprising:
    i) about 1.8% w/w of the phenolic biocide;
    ii) about 1.0% w/w of the choline salt; and
    iii) about 97.2% w/w of a non-aqueous vehicle.

11. A topical medicament as claimed in claim 5, comprising:
    i) about 1.8% w/w of the phenolic biocide;
    ii) about 1.0% w/w of the choline salt;
    iii) about 1.8% w/w of the surfactant; and
    iv) about 95.4% w/w of a non-aqueous vehicle.

12. A topical medicament as claimed in claim 5, comprising:
    i) about 1.8% w/w of the phenolic biocide;
    ii) about 1.0% w/w of the choline salt;
    iii) about 1.8% w/w of the surfactant;
    iv) about 0.5% w/w cetrimide;
    v) about 0.25% w/w Myo-inositol; and
    vi) about 94.65% w/w of a non-aqueous vehicle.

13. A topical medicament as claimed in claim 4, comprising:
    i) 1.8 g hexylresorcinol;
    ii) 1.0 g choline chloride; and
    iii) 97.2 g White Vaseline.

14. A topical medicament as claimed in claim 5, comprising:
    i) 1.8 g hexylresorcinol;
    ii) 1.0 g choline chloride;
    iii) 1.8 g N-lauroylsarcosine sodium; and
    iv) 95.4 g White Vaseline.

15. A topical medicament as claimed in claim 5, comprising:
    i) 1.8 g hexylresorcinol;
    ii) 1.8 g N-lauroylsarcosine;
    iii) 0.5 g cetrimide;
    iv) 1.0 g choline chloride;
    v) 0.25 g Myo-inositol; and
    vi) 94.65 g White Vaseline.

* * * * *

UNITED STATES PATENT AND TRADEMARK OFFICE
CERTIFICATE OF CORRECTION

PATENT NO.     : 6,469,070 B1
DATED          : October 22, 2002
INVENTOR(S)    : Dirk Vanden Berghe It is certified that error appears in the above-identified patent and that said Letters Patent is hereby corrected as shown below:

Column 1,
Line 65, "w/w" should read -- w/w. --.

Signed and Sealed this

Tenth Day of June, 2003

JAMES E. ROGAN
*Director of the United States Patent and Trademark Office*